(12) United States Patent
Fine et al.

(10) Patent No.: US 7,386,336 B2
(45) Date of Patent: Jun. 10, 2008

(54) METHOD AND SYSTEM FOR USE IN NON-INVASIVE OPTICAL MEASUREMENTS OF BLOOD PARAMETERS

(75) Inventors: Ilya Fine, Rehovot (IL); Alexander Finarov, Rehovot (IL)

(73) Assignee: ORSENSE Ltd., Rehovot (IL)

(*) Notice: Subject to any disclaimer, the term of this patent is extended or adjusted under 35 U.S.C. 154(b) by 0 days.

(21) Appl. No.: 11/341,631

(22) Filed: Jan. 30, 2006

(65) Prior Publication Data
US 2006/0129040 A1 Jun. 15, 2006

Related U.S. Application Data

(63) Continuation of application No. 10/452,932, filed on Jun. 3, 2003, now Pat. No. 6,993,372.

(51) Int. Cl.
*A61B 5/1455* (2006.01)
(52) U.S. Cl. .............. 600/335; 600/310; 600/340
(58) Field of Classification Search ............... 600/310, 600/322, 335, 340, 344, 331
See application file for complete search history.

(56) References Cited

U.S. PATENT DOCUMENTS

| | | | |
|---|---|---|---|
| 5,057,695 A | 10/1991 | Hirao et al. | |
| 5,069,214 A | 12/1991 | Samaras et al. | |
| 5,152,296 A | 10/1992 | Simons | |
| 6,049,727 A * | 4/2000 | Crothall ............. | 600/310 |
| 6,149,588 A * | 11/2000 | Noda et al. ........... | 600/316 |
| 6,213,952 B1 | 4/2001 | Finarov et al. | |
| 6,222,189 B1 | 4/2001 | Misner et al. | |
| 6,285,894 B1 | 9/2001 | Oppelt et al. | |
| 6,400,972 B1 | 6/2002 | Fine | |
| 6,461,305 B1 | 10/2002 | Schnall | |
| 6,587,704 B1 * | 7/2003 | Fine et al. ............ | 600/335 |
| 6,801,798 B2 | 10/2004 | Geddes et al. | |
| 6,983,178 B2 | 1/2006 | Fine et al. | |
| 2004/0225205 A1 * | 11/2004 | Fine et al. ........... | 600/316 |

FOREIGN PATENT DOCUMENTS

| | | |
|---|---|---|
| WO | WO 99/65384 A1 | 12/1999 |
| WO | WO 01/26539 A1 | 4/2001 |
| WO | WO 01/45553 A1 | 6/2001 |
| WO | WO 01/67946 A1 | 9/2001 |
| WO | WO 01/96872 A2 | 12/2001 |

\* cited by examiner

*Primary Examiner*—Eric Winakur
*Assistant Examiner*—Etsub D Berhanu
(74) *Attorney, Agent, or Firm*—Browdy and Neimark (57) ABSTRACT

A method and device are presented for use in non-invasive optical measurements of at least one desired characteristic of patient's blood. A condition of artificial blood kinetics is created at a measurement location in a patient's blood perfused fleshy medium and maintained for a certain time period. This condition is altered over a predetermined time interval within said certain time period so as to modulate scattering properties of blood. Optical measurements are applied to the measurement location by illuminating it with incident light beams of at least two different wavelengths in a range where the scattering properties of blood are sensitive to light radiation, detecting light responses of the medium, and generating measured data indicative of time evolutions of the light responses of the medium for said at least two different wavelengths, respectively, over at least a part of said predetermined time interval.

8 Claims, 7 Drawing Sheets

METHOD AND SYSTEM FOR USE IN NON-INVASIVE OPTICAL MEASUREMENTS OF BLOOD PARAMETERS

FIELD OF THE INVENTION

This invention is generally in the field of non-invasive optical measurement techniques for measuring blood-related parameters, and relates to an optical probe to be applied to a patient's finger or toe and a method of operating the probe.

BACKGROUND OF THE INVENTION

Non-invasive techniques for measuring various blood parameters, e.g., blood oxygen saturation, have become very popular, since they do not require the withdrawal of a blood sample from a patient's body. Optical monitoring techniques of the kind specified utilize the detection of light transmitted or reflected from the location on the patient's body under measurement, and are based on spectrophotometric measurements enabling the indication of the presence of various blood constituents based on known spectral behaviors of these constituents.

Most of these techniques utilize a measurement optical device or probe, designed in a manner to be attached to the patient's finger, which includes an optical assembly for irradiating the finger with light and detecting its light response. The conventional devices of the kind specified, such as a pulse oximeter, which is the generally accepted standard of everyday clinical practice, provide for measuring enhanced optical pulsatile signals caused by the changes in the volume of a blood flowing through a fleshy medium (e.g., finger).

It is known that for blood parameters other than oxygen saturation, e.g., glucose concentration, significant difficulties have been accoutered, because their absorption spectral behavior in red and near infrared regions is not as remarkable as for the oxygenized hemoglobin. Hence, the main limitations on the way of expanding the non-invasive techniques to the measurements different from pulse oximetry are associated with the limited selectivity of the absorption based method.

A different technique is disclosed in U.S. Pat. No. 6,400,972, WO 01/45553 and WO 01/96872, all assigned to the assignee of the present application. This is an occlusion-based technique, according to which an over-systolic pressure is applied to the blood perfused fleshy medium with a normal blood flow so as to create a state of temporary blood flow cessation at the measurement location. The measurement with different wavelengths of incident radiation and/or different polarization states of detected light are carried out at timely separated sessions taken during a time period including a cessation time when the state of the blood flow cessation is maintained. This technique utilizes the condition of the "artificial blood kinetics" rather than the natural blood kinetics taking place when the state of the total blood cessation is not achieved. As a result of the cessation of the blood flow, a condition of the artificial kinetics is achieved with the optical characteristics of the blood associated with the light response being different from those at the natural blood kinetics. Indeed, it is known that the scattering properties of blood depend on the size and shape of scatterers (aggregates). Thus, time changes of the light response at the condition of artificial kinetics depend on the changes in the shape and average size of the scattering centers in the medium, i.e., red blood cells (RBC) aggregation (Rouleaux effect). It was found that owing to the effect of the artificial kinetics, the optical characteristics of blood changes dramatically, such that they differ from those of the fleshy medium with a normal blood flow by about 25 to 45%, and sometimes even by 60%. Hence, the accuracy (i.e., signal-to-noise ratio) of the technique based on the artificial kinetics as well as selectivity of the optical measurements can be substantially better when compared with those based on measurements of the blood parameters at natural kinetics.

Various probe devices suitable for the occlusion-based measurements are described in U.S. Pat. No. 6,213,952 and US 2002/0173709 both assigned to the assignee of the present application. These devices are designed to apply over-systolic pressure to the patient's finger at a location upstream of a measurement location in the finger, with respect to the direction of normal blood flow, thereby creating a state of blood flow cessation at the measurement location. Generally, the device includes a clip member for securing the patient's finger between its two clamping arms that also serve for carrying the optics of a measurement unit, and includes a pressurizing assembly outside the clip member for applying over-systolic pressure.

SUMMARY OF THE INVENTION

There is a need in the art to facilitate non-invasive measurements of blood-related characteristics by providing novel method, probe device and system for non-invasive, occlusion-based measurements applied to a patient's blood perfused fleshy medium, e.g., finger or toe.

The technique of the present invention takes advantage of the above-described occlusion-based measurements, namely is based on creating and controlling the artificial blood kinetics in a patient's blood perfused fleshy medium and applying optical measurements thereto. The condition of artificial kinetics is created and maintained for a certain time period, and is controllably altered over a predetermined time interval within said certain time period. The condition of artificial kinetics is created by applying a primary over-systolic pressure to a certain location at the medium with a normal blood flow so as to achieve a state of temporary blood flow cessation at the medium at a measurement location. The location of application of the primary pressure is either upstream of the measurement location with respect to the normal blood flow direction in the medium or in the vicinity of the measurement location. The control of the condition of the artificial kinetics is achieved by applying a perturbation of a secondary pressure to the fleshy medium, either downstream of the location of the primary pressure application or substantially at the same location. The physical effect of the secondary pressure results in the modification of the aggregates of red blood cells (RBC). Therefore, the location of the applying of the secondary pressure has to be in the vicinity of the measurement location.

The non-invasive optical measurements are carried out by illuminating a measurement location on the medium with incident light beams of at least two different wavelengths in a range where the scattering or absorbing properties of blood are sensitive to light radiation (e.g., in red through near infrared (NIR) range). The optical determination of blood characteristics is carried out over a predetermined time interval when the condition of artificial blood kinetics is controllably altered. This predetermined time interval is within the time period during which the over-systolic pressure is applied.

Thus, according to one broad aspect of the invention, there is provided a method for use in non-invasive optical measurements of at least one desired characteristic of patient's blood, the method comprising:

(a) creating a condition of artificial blood kinetics at a measurement location in a patient's blood perfused fleshy medium and maintaining this condition for a certain time period;

(b) altering said condition of artificial blood kinetics at the measurement location over a predetermined time interval within said certain time period so as to modulate scattering properties of blood; and (c) applying optical measurements to the measurement location by illuminating it with incident light beams of at least two different wavelengths in a range where the scattering properties of blood are sensitive to light radiation, detecting light responses of the medium, and generating measured data indicative of time evolutions of the light responses of the medium for said at least two different wavelengths, respectively, over at least a part of said predetermined time interval.

According to another broad aspect of the invention there is provided a method for use in non-invasive optical measurements of at least one desired characteristic of patient's blood, the method comprising:

applying a primary over-systolic pressure to a patient's blood perfused fleshy medium at a location in vicinity of a measurement location to thereby create a condition of artificial blood kinetics at the measurement location, and maintaining this condition for a certain time period;

varying the over-systolic pressure in the vicinity of the measurement location starting from said primary over-systolic pressure value thereby altering said condition of artificial blood kinetics at the measurement location over a predetermined time interval within said certain time period so as to modulate scattering properties of blood; and applying optical measurements to the measurement location by illuminating it with incident light beams of at least two different wavelengths in a range where the scattering properties of blood are sensitive to light radiation, detecting light responses of the medium, and generating measured data indicative of time evolutions of the light responses of the medium for said at least two different wavelengths, respectively, over at least a part of said predetermined time interval.

According to yet another broad aspect of the present invention, there is provided an optical system for use in non-invasive optical determination of at least one desired characteristic of patient's blood, the system comprising:

(A) a probe including: (i) an optical measuring unit operable for illuminating a measurement location on a patient's blood perfused flesh medium with different wavelengths of incident light, detecting light responses of the medium, and generating measured data indicative of time evolutions of the light responses of the medium corresponding to the different wavelengths of incident light, respectively; and (ii) a pressurizing assembly operable for applying pressure to the patient's fleshy medium;

(B) a control unit connectable to said measuring unit and said pressurizing assembly for synchronizing the operation thereof so as to apply a primary over-systolic pressure to a certain location on the medium to create a condition of artificial blood kinetics in the medium at the measurement location and maintain this condition for a certain time period, to apply a secondary controllably varying pressure to the fleshy medium in the vicinity of the measurement location so as to alter said condition of artificial blood kinetics over a predetermined time interval within said certain time period thereby modulating scattering properties of blood, and to apply the optical measurements while altering the condition of the artificial blood kinetics, the control unit comprising: (a) a memory for storing reference data sensitive to patient individuality and indicative of the desired blood characteristic as a function of a parameter derived from scattering spectral features of the medium, and (b) a data acquisition and processing utility coupled to output of the measuring unit for receiving and analyzing the measured data to utilize the reference data and determine said at least one desired blood characteristic.

According to one embodiment of the invention, the altering of the condition of the artificial blood kinetics is performed by applying a perturbation to the medium by a secondary pressure pulse of a predetermined value over the predetermined time interval so as to modulate scattering properties of blood.

According to one example, the secondary pressure can be applied to the medium (e.g., patient's finger) at the location of the main occlusion providing the over-systolic pressure. In this case, the secondary pressure is varied starting from said primary over-systolic pressure value and reaching higher values.

According to another example, the secondary pressure can be applied to the medium at a certain location selected downstream of the main occlusion with respect to the blood flow direction. In this case, the secondary pressure may vary from zero to over-systolic pressure values that may be higher than the primary over-systolic pressure. The location of the applying of the secondary pressure may either coincide with the location of a light detector or slightly differ from it, depending on the kind of measured medium and/or design of the measurement probe.

It should be appreciated that a modification of RBC clusters resulting in the altering of the artificial kinetics can be caused by many different ways. Thus, other than the single secondary pulse described above, the altering of the condition of artificial blood kinetics can be carried out by applying a perturbation to the medium by means of the secondary pressure of a predetermined cyclic pattern over the predetermined time interval.

According to the invention, the detection of the light responses of the medium for the purpose of determining the desired blood characteristics is carried out during the altering of the condition of the artificial blood kinetics. For example, for the case when one secondary pulse was applied to the medium, the measured data indicative of time evolutions of the light responses of the medium for at least two different wavelengths over the time interval that starts when step pulse of the secondary pressure has been applied and onward can be used for the determining of the blood characteristics. Likewise, for the case when a series of pulses have been applied to the medium, the measured data of the light responses over at least one time interval selected from the intervals when the secondary pressure pulse was applied can be used for the determining of the blood characteristics. Moreover, the measured data over at least one interval selected from the intervals after the release of the secondary pressure can also be utilized for the determining of the blood characteristics.

According to the invention, a parameter derived from scattering spectral features of the medium during the altering of the condition of the artificial blood kinetics is used for the determination of blood characteristics. According to one example, this parameter is a parametric slope (PS) defined as a ratio between a first function depending on a light response of the medium corresponding to one wavelength and a second function depending on the light response of the medium corresponding to another wavelength.

According to one embodiment, the first and second functions can be logarithmic functions $\log(T_1)$ and $\log(T_2)$ of the light responses $T_1$ and $T_2$ corresponding to the two different wavelengths $\lambda_1$ and $\lambda_2$, respectively. According to another embodiment, the first and second functions can be functions of the time rate of the changes of the light response signal, i.e., $\Delta T/\Delta t$ (or $\Delta \log T/\Delta t$), where $\Delta t$ can be any part of the time interval during which the condition of artificial kinetics is changed.

According to the invention, for determination of a desired blood characteristic a reference data sensitive to patient individuality should be provided. The reference data should be indicative of the desired blood characteristic as a function of the parameter derived from scattering spectral features of the medium. Such reference data can, for example, be a calibration curve defining a dependence of the PS on the desired blood characteristic. The calibration curve can be created by plotting a dependence of the PS versus the desired blood characteristic that can be obtained for the particular individual by any other known method, independent of the current measurements. It should be appreciated that for different blood characteristics the independent methods may also be different.

The measuring system of the present invention comprises such main constructional parts as a probe and a control unit.

According to one embodiment, the probe includes a pressurizing assembly and a measuring unit. The pressurizing assembly includes a primary occlusion cuff for applying the primary over-systolic pressure to the medium, a secondary occlusion cuff for applying the secondary pressure to the medium and a pressure driver actuated by the control unit for operating the squeezing of the cuffs and. According to this embodiment, the location secondary occlusion cuff is selected downstream of the location primary occlusion cuff with respect to the normal blood flow direction. The measuring unit comprises an illumination assembly and a light collection/detection assembly. The illumination assembly includes a plurality of light sources (e.g., LEDs) associated with a suitable drive mechanism operated by the control unit. Alternatively, a single broad band illuminator can be used. The light sources generate incident radiation propagating through the medium at a measurement location. The light collection/detection assembly includes one or more frequency selective detectors arranged near the measurement location. Examples of collection/detection assembly include, but are not limited to, spectrophotometers and/or photodiodes typically equipped with frequency selective filters and amplifying means, which are not specifically shown. It should be noted that the measurement location may, for example, be accommodated so as to coincide with the location of applying the secondary pressure or slightly differ from it, depending on the kind of measured medium and/or design of the measurement probe.

The optical measurements are carried out to detect the light transmitted through the medium (or the light reflected therefrom, as the case may be), and to generate data representative thereof (constituting measured data). In the present example, the light transmitted through the medium is detected (constituting the light response of the medium).

According to another embodiment of the invention, the probe has a substantially ring-like shape that is formed by two substantially U-shape parts configured for enclosing and holding a portion of the medium therebetween. These U-shape parts can partially overlap over a predetermined distance. The pressure applied to the finger should be sufficient to case total cessation of the blood flow in the finger downstream of the occlusion (i.e., the place where the pressure is applied). The pressurizing assembly may include an air cushion mounted on an inner side of at least one of the U-shaped portions and connected to a driver operable by the control unit to apply a controllable variable pressure to the portion of the medium enclosed between the two U-shaped parts. Alternatively, the pressurizing assembly may include a cuff associated with a pressure drive operable to move either one of the semi-rings towards one another, and thereby apply pressure to the finger portion enclosed therebetween. An example of the pressure drive includes, but is not limited to a wind-up spring coupled with the cuff. Squeezing of the cuff can provide a movement of the semi-rings to each other, and thereby provide continues variation of the pressure applied to the finger. With the ring-like configuration of the probe, the primary over-systolic pressure as well as the secondary pressure is applied by the same pressurizing assembly. Therefore, the location of the main occlusion (primary pressure) causing the creation of the condition of artificial kinetics (a blood flow cessation state) coincides with the location at which the artificial blood kinetics is altered (application of secondary pressure).

The probe of this embodiment further comprises the measuring unit configured for illuminating a measurement location on the portion of the finger with incident light beams, detecting light responses of the medium, and generating measured data indicative of time evolutions of the light responses of the blood. For this purpose, the measuring unit includes an illumination assembly and a light collection/detection assembly. The illumination assembly can include a plurality of light sources (e.g., LEDs) with a suitable drive mechanism operated by the control unit. Alternatively, a single broad band illuminator can be used. The light sources radiate the measurement location of the finger through an aperture arranged in one of the semi-ring to provide unobstructed optical transmission to the surface of the fleshed medium. The light collection/detection assembly includes a detector that can receive the light radiation transmitted through the medium. Alternatively, the detector unit may include an array (generally, at least two) light detectors arranged in a spaced-apart relationship along the circumference of the finger within the measurement location.

The collection/detection assembly of the probe is coupled to the control unit via a suitable electronic block, typically including an analog to digital (A/D) converter (not shown). The control unit is interconnected between the measuring unit and the pressurizing assembly of the probe for operating the corresponding pressure and light sources drivers, and is coupled to the output of the detection assembly to be responsive to the measured data. The control unit includes a data acquisition and processing utility having a computer device having such known utilities as a processor, a memory for storing, inter alia, reference data (RD) and a monitor. The processor is preprogrammed by a suitable software model capable of analyzing the received output of the detection assembly (measured data) and determining one or more desired characteristics of the patient's blood, as have been described above.

Thus, according to yet another aspect of the invention, there is provided a probe for use in non-invasive optical measurements of blood-related parameters, the probe including:

(A) two substantially U-shaped portions configured for enclosing and holding a portion of a patient's blood perfused flesh medium therebetween, (B) a measuring unit operable for illuminating a measurement location on the portion of the medium with different wavelengths of incident light beams, detecting light responses of the medium, and generating measured data indicative of time evolutions of the light responses of the medium corresponding to the different wavelengths of incident light, respectively; and (C) a pressurizing assembly associated with one of the U-shaped portions and operable for applying a primary over-systolic pressure to the fleshy medium so as to create a condition of artificial blood kinetics in the fleshy medium and maintain this condition for a certain time period; and for applying a secondary controllably varying over-systolic pressure to the fleshy medium, so as to alter said condition of artificial blood kinetics over a predetermined time interval within said certain time period, thereby to modulate scattering properties of blood.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

The principles and operation of the system and method for non-invasive optical measurement of blood parameters according to the present invention may be better understood with reference to the drawings and the accompanying description, it being understood that these drawings and examples in the description are given for illustrative purposes only and are not meant to be limiting. The same reference Roman numerals and alphabetic characters will be utilized for identifying those components which are common in the system for non-invasive optical measurement of blood parameters shown in the drawings throughout the present description of the invention.

According to one general aspect, the present invention provides a novel method and system for non-invasive optical determination of blood characteristics. Examples of the blood characteristics include, but are not limited to concentration of a substance in patient's blood (e.g., glucose, hemoglobin), oxygen saturation, Erythrocyte Sedimentation Rate (ESR) and Erythrocyte Aggregation Rate (EAR). The method is based on creating and controlling the artificial blood kinetics in a patient's blood perfused fleshy medium, e.g., his finger, and applying optical measurements thereto. The condition of artificial kinetics is created and maintained for a certain time period. The condition of artificial kinetics is preferably created by applying a primary over-systolic pressure to a certain location at the medium with a normal blood flow so as to achieve a state of temporary blood flow cessation. The control of the condition of the artificial kinetics is achieved by applying a perturbation of a secondary pressure to the fleshy medium, as will be described in detail hereinbelow.

The non-invasive optical measurements are carried out by illuminating a measurement location on the medium with incident light beams of at least two different wavelengths in a range where the scattering or absorbing properties of blood are sensitive to light radiation (e.g., in red through near infrared (NIR) range).

Figure 1:
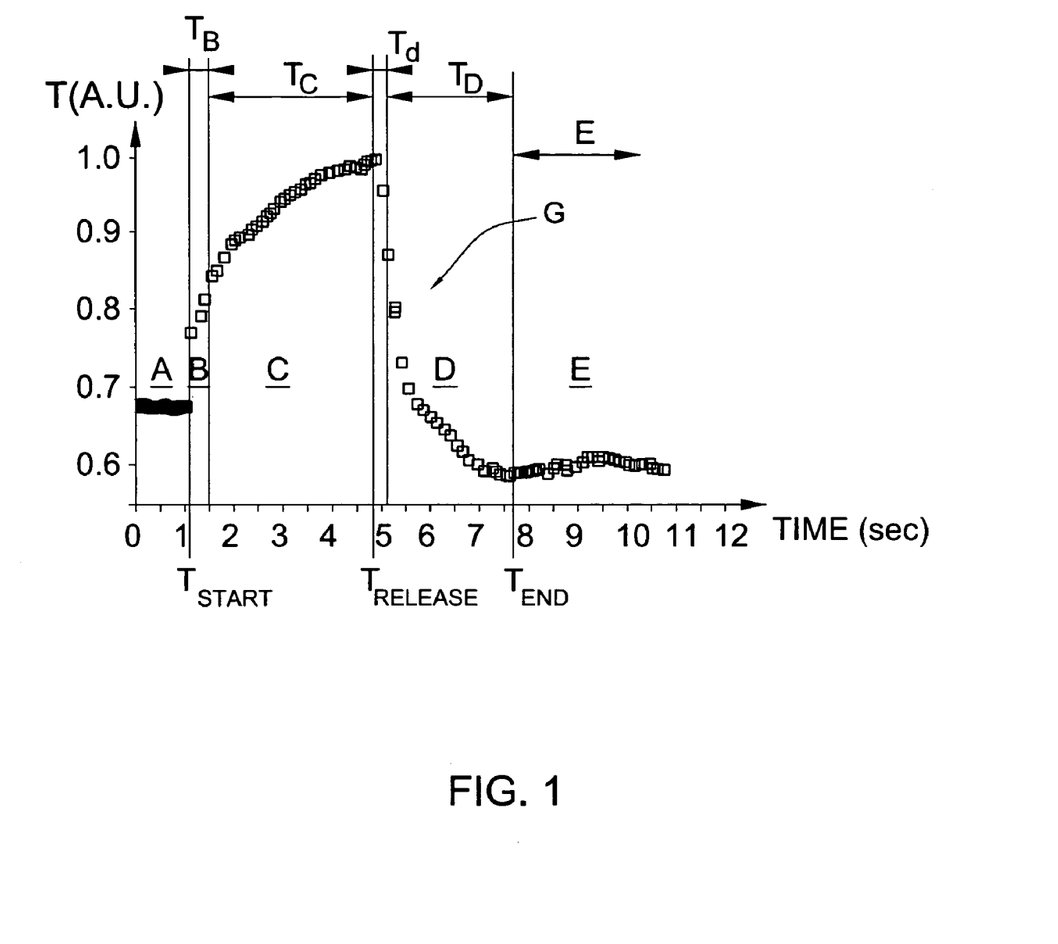
FIG. 1 illustrates a typical plot representing light transmission characteristics of blood obtained by when the condition of artificial kinetics is created.

Referring now to the drawings, FIG. 1 illustrates an example showing a typical plot representing light transmission characteristic (light responses) of blood obtained over the time interval when the condition of artificial kinetics is created, maintained during a certain cessation time, and then released. In particular, the plot shows how the light-transmitting characteristic of blood changes under the application and release of the primary over-systolic pressure. The transmitting characteristics are shown in FIG. 1 (and in the further drawings) as the so-called "Relative Transmission", i.e., in Transmission Arbitrary Units or T(A.U.).

The application of primary pressure to the fleshy medium starts at a moment $T_{start}$, and is maintained for a period of time such as not to cause irreversible changes in the medium (e.g., 4 seconds). The pressure is released at the moment $T_{release}$. Measurements of the Relative Transmission are performed continuously, starting prior to the application of the over-systolic pressure. Different regions of light responses of the medium, designated A, B, C, D and E, corresponding to the different states of the blood flow are observed. Region A corresponds to a state of normal blood flow before the over-systolic pressure is applied. As shown, this region is characterized by a standard fluctuating value of the relative light transmission of blood. Region B starts at moment $T_{start}$ (when the pressure is initially applied) and maintains over a short period of time $T_B$ (about 0.5 sec) following the actual start of the condition of artificial blood kinetics. Measurements taken over this time period are not steady and can be disregarded, due to the unavoidable influence of motional and/or other artifacts causing non-monotonic fluctuations of the light transmission. Region C corresponds to a state of the temporary cessation of blood flow, which lasts within a cessation time $T_C$ between a moment determined as $(T_{start}+T_B)$ and the moment $T_{release}$. During this cessation time $T_C$ the ascending curve (as shown in FIG. 1) or descending curve (not shown), depending on the incident wavelength of relative light transmission of blood, can be observed. It should be noted that this is the region where the condition of artificial kinetics is maintained over $T_C$. Generally, the light transmission curve can reach an asymptotic maximum over one second to several minutes. Region D corresponds to a transitional state of blood flow, which takes place after releasing the over-systolic pressure. This state starts with a slight delay $T_d$ (approximately 0.5 sec), i.e., at the moment determined as $(T_{release}+T_d)$. During the time period $T_D$ of the duration of region D, the relative transmission of blood monotonously descends until it reaches values characteristic of the normal blood flow. Such a moment is marked as $T_{end}$ in the drawing. Usually, the end of region D, and the beginning of region E, is detected when the changes of the light transmission become periodic and minimal (about 2%). Region E corresponds to a state of the normal blood flow, which is similar to that in region A. This technique is disclosed in the above-indicated patent publications, assigned to the assignee of the present application.

According to the present invention, the optical determination of blood characteristics is carried out over a predetermined time interval when the condition of artificial blood kinetics is controllably altered. This predetermined time interval is within the time period during which the primary over-systolic pressure is maintained.

According to one embodiment of the invention, the altering of the condition of the artificial blood kinetics is performed by applying a perturbation to the medium by a secondary pressure pulse of a predetermined value over the predetermined time interval so as to modulate scattering properties of blood. According to one example, the secondary pressure can be applied to the medium (e.g., patient's finger) at the location of the main occlusion providing the over-systolic pressure. According to another example, the secondary pressure can be applied to the medium at a certain location selected downstream of the main occlusion with respect to the blood flow direction. It should be noted that the location of the applying of the secondary pressure may either coincide with the location of a light detector or slightly differ from it, depending on the kind of measured medium and/or design of the measurement probe. The physical effect of the secondary pressure results, inter alia, in the modification of the aggregates of red blood cells (RBC). Therefore, the location of the applying of the secondary pressure has to be in the vicinity of the measurement place.

Figure 2:
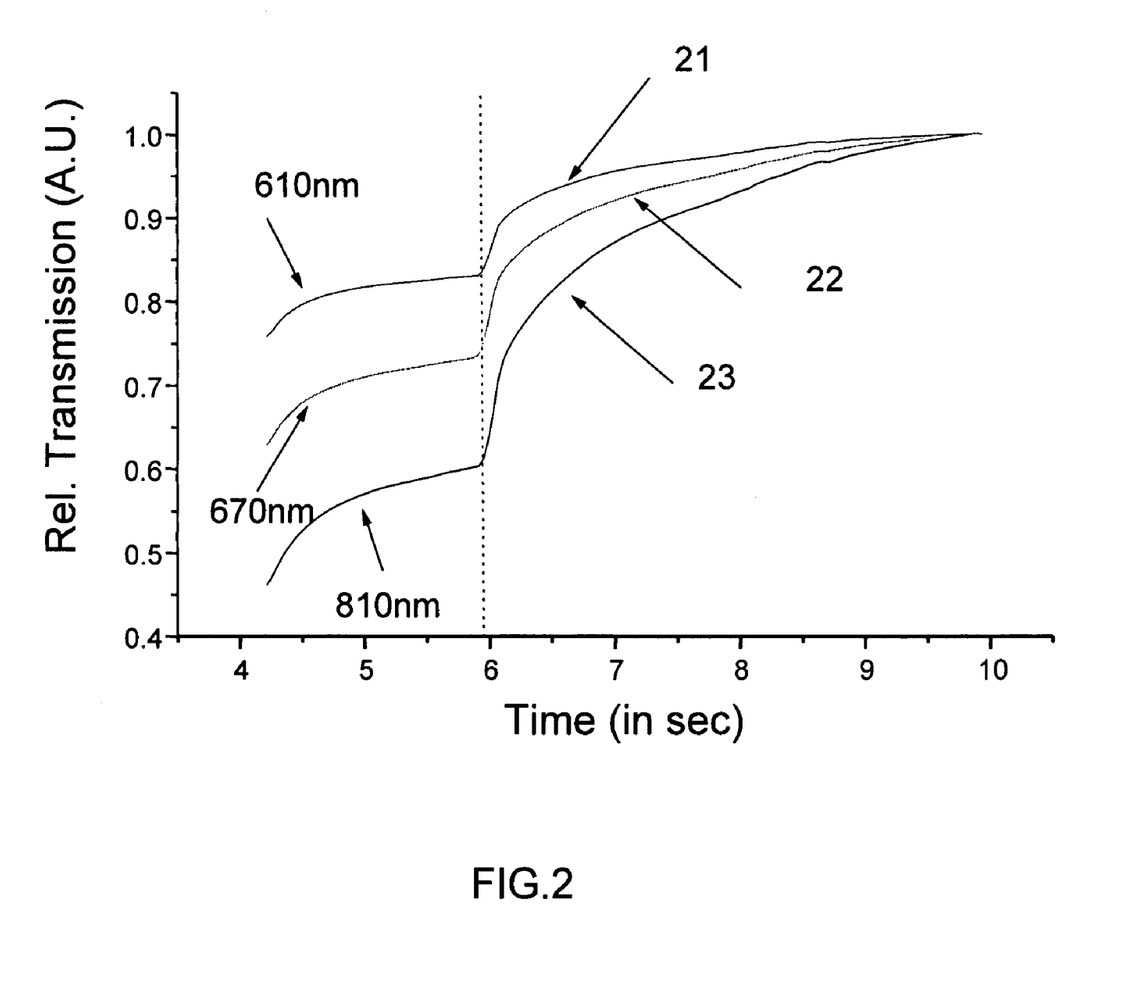
FIG. 2 illustrates a plot showing three examples of the time dependency of light transmission characteristics of blood experimentally obtained for three different wavelengths when the condition of artificial kinetics is altered by a perturbation of a secondary pressure step pulse applied to the medium.

FIG. 2 illustrates a plot showing three examples (curves 21, 22 and 23) of the time dependency of light transmission characteristics of blood experimentally obtained for three different wavelengths (namely, $\lambda_1$=610 nm, $\lambda_2$=670 nm and $\lambda_3$=810 nm) when the condition of artificial kinetics is altered by a perturbation of a secondary pressure step pulse applied to the medium.

The application of the primary over-systolic pressure (for example, higher than 180 mmHg) to the fleshy medium starts at a certain time moment ($t_{start}$=0 sec as shown in FIG. 2), and is maintained as long as desired (16 sec in FIG. 2). Preferably, the duration of the applying of the primary pressure is stipulated by the condition to bring about the artificial blood kinetics without causing irreversible changes in the medium. Then, the step pulse of the secondary pressure (about 300 mmHg) is applied at the time moment of $t_{sec}\approx4$ sec that is reflected by a bend of the curves 21, 22 and 23 at the time kick point $t_{sec}$.

It should be noted that the predetermined value of the secondary pressure pulse can, for example, be in the range of about 0-300 mmHg. It was found by the inventors that one can obtain some more useful information about the patient's blood characteristics by means of manipulating the magnitude of the secondary pressure pulse. In particular, in the case when the magnitude of the secondary pressure pulse is small and does not exceed a certain relatively small value $P_1$, all three main components of the blood (venous, capillary and arterial blood components) can provide contribution in the measurements. However, in the case when the magnitude of the secondary pressure would exceed the value of $P_1$ the venous blood component can be excluded from the consideration. Likewise, in order to exclude from the consideration also the capillary blood component the secondary pressure should exceed the value of $P_2$ (where $P_2>P_1$). In other words, when the magnitude of the secondary pressure is over $P_2$ venous and capillary blood becomes forced out of the measurement location, while arterial blood remains at the measurement location, and measurements in this case would be applied to arterial blood only. It should be understood that the values of $P_1$ and $P_2$ depend on the person's physiology, and should be selected individually for each patient. It should be appreciated that a modification of RBC clusters resulting in the altering of the artificial kinetics can be caused by many different ways. Thus, other than the single secondary pulse described above, the altering of the condition of artificial blood kinetics can be carried out by applying a perturbation to the medium by means of the secondary pressure of a predetermined cyclic pattern over the predetermined time interval. The cyclic pattern can be a series of shot pressure pulses having amplitudes in the range of about 0-300 mmHg.

Figure 3:
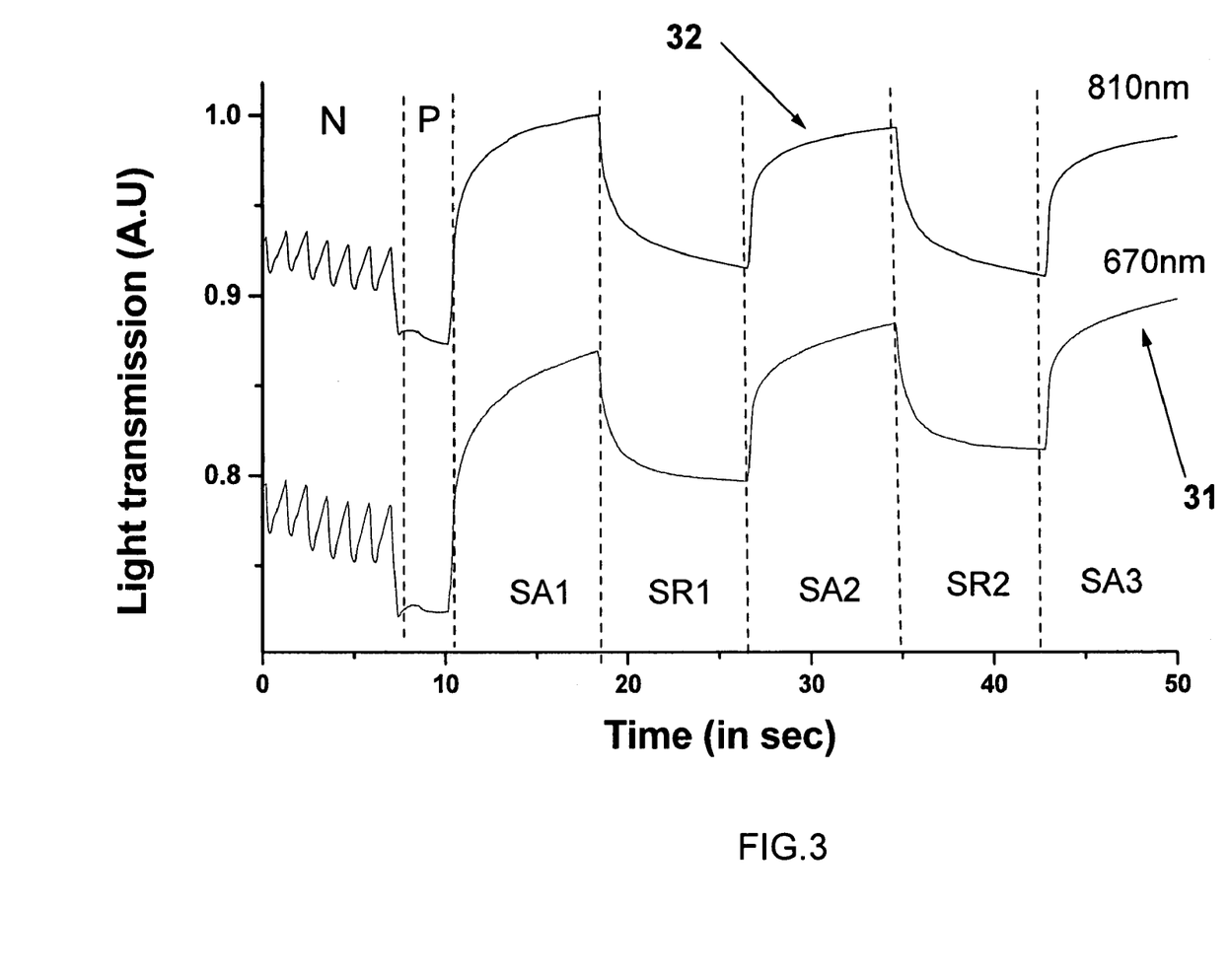
FIG. 3 illustrates a plot showing three examples of the time dependency of light transmission characteristics of blood experimentally obtained for two different wavelength when the condition of artificial kinetics is altered by a perturbation of the medium by a series of shot pressure pulses.

FIG. 3 illustrates a plot showing three examples (curves 31 and 32) of the time dependency of light transmission characteristics of blood experimentally obtained for three different wavelengths (namely, $\lambda_1$=670 nm and $\lambda_2$=810 nm) when the condition of artificial kinetics is altered by a perturbation of the medium by a series of shot secondary pressure pulses. In the example shown in FIG. 3, the duration of the secondary pressure pulses is 1.5 s while the amplitude is in the range of about 220-300 nm Hg. It should be appreciated that in practice the magnitudes of the pulse duration and amplitude depend on the particular patient and configuration of the measurement system.

Different regions of light responses of the medium, designated N, P, SA1, SR1, SA2, SR2, etc. corresponding to the different states of the blood flow, are observed. Region N is analogous to region A in FIG. 1, and corresponds to a state of normal blood flow before the over-systolic pressure is applied. As shown, this region is characterized by a standard fluctuating value of the relative light transmission of blood. Region P starts at the time moment when the primary over-systolic pressure is applied to the medium ($t_{start}$=8 sec in FIG. 3) and continues until the perturbation of the medium by a first secondary pressure pulse ($t_{sa1}$=10.5 sec in FIG. 3). The first secondary pressure pulse is applied over 8.5 sec (region SA1) and released at the time moment $t_{sr1}$=19 sec that is reflected by a decrease of the light transmission curve over 7 sec (region SR1). Thereafter, a second secondary pressure pulse ($t_{sa2}$=26 sec in FIG. 3) is applied over 9 sec (region SA2), which is released at the time moment $t_{sr2}$=35 sec (region SR2). It should be noted that application of the secondary pressure pulses can continue as long as desired over the time period when the over-systolic pressure is applied.

According to the invention, the detection of the light responses of the medium for the purpose of determining the desired blood characteristics is carried out during the altering of the condition of the artificial blood kinetics. For example, for the above case corresponding to FIG. 2, the measured data indicative of time evolutions of the light responses of the medium for at least two different wavelengths over the time interval that starts when step pulse of the secondary pressure has been applied and onward can be used for the determining of the blood characteristics. Likewise, for the case corresponding to FIG. 3, the measured data of the light responses over at least one time interval selected from the intervals when the secondary pressure pulse was applied (i.e., any interval selected from intervals SA1, SA2, etc.) can be used for the determining of the blood characteristics. Moreover, the measured data over at least one interval selected from the intervals after the release of the secondary pressure (i.e., any interval selected from intervals SR1, SR2, etc.) can also be utilized for the determining of the blood characteristics.

According to the invention, a parameter derived from scattering spectral features of the medium during the altering of the condition of the artificial blood kinetics is used for the determination of blood characteristics. According to one example, this parameter is a parametric slope (PS) defined as a ratio between a first function depending on a light response of the medium corresponding to one wavelength and a second function depending on the light response of the medium corresponding to another wavelength.

According to one embodiment, the first and second functions can be logarithmic functions $\log(T_1)$ and $\log(T_2)$ of the light responses $T_1$ and $T_2$ corresponding to the two different wavelengths $\lambda_1$ and $\lambda_2$, respectively. According to another embodiment, the first and second functions can be functions of the time rate of the changes of the light response signal, i.e., $\Delta T/\Delta T$ (or $\Delta \log T/\Delta t$), where $\Delta t$ can be any part of the time interval during which the condition of artificial kinetics is changed.

Figure 4:
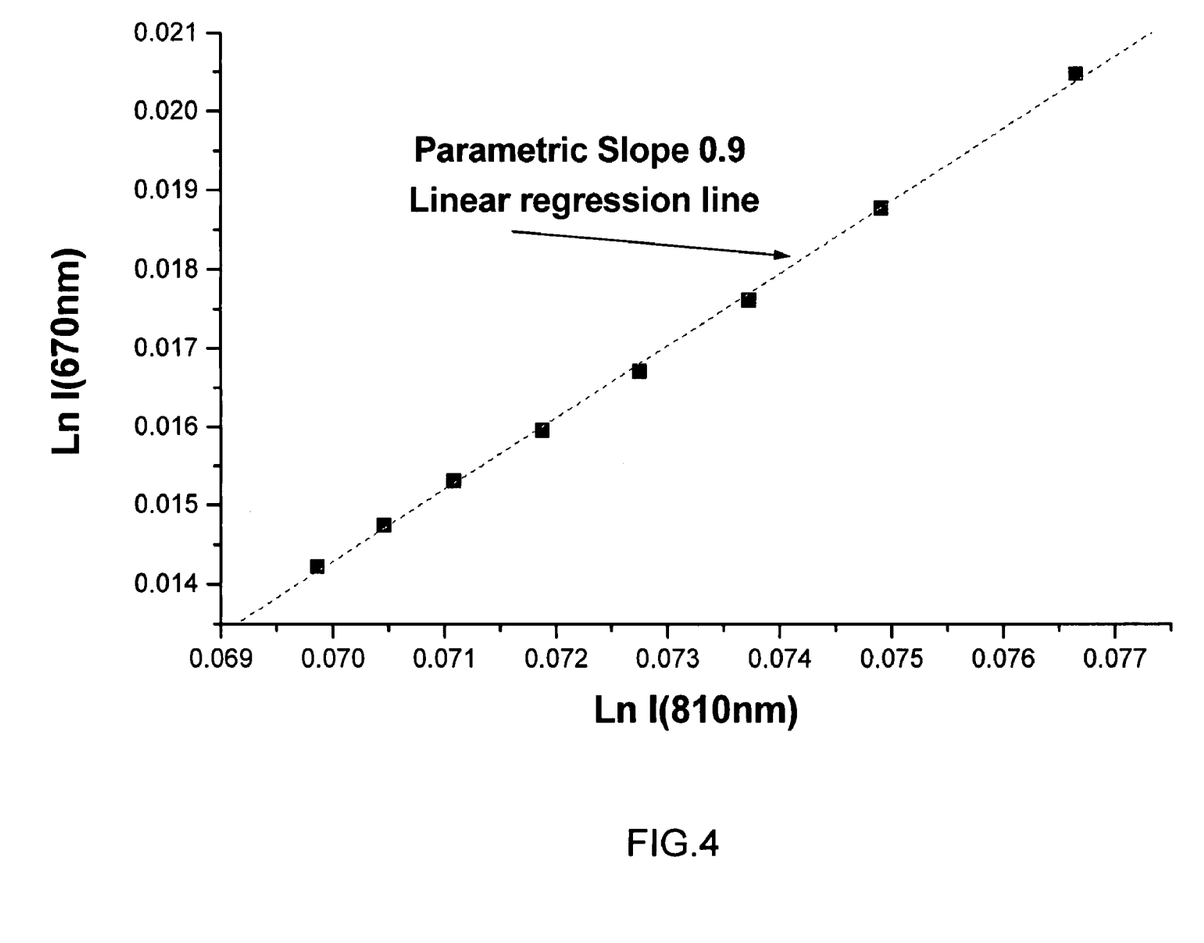
FIG. 4 illustrates a relationship between the natural logarithm of the light response of the medium at one wavelength $\lambda_1$ and natural logarithm of the light response at the other wavelength.

Referring to FIG. 4, an exemplary plot showing a relationship between the natural logarithm of the light response $\ln(T_1)$ of the medium at the wavelength $\lambda_1$=670 nm and the natural logarithm of the light response $\ln(T_2)$ at the wavelength $\lambda_2$=810 nm. The measurements were obtained when the condition of artificial kinetics is altered by a perturbation of the medium by a first secondary pressure pulse, i.e., over interval SA1 shown in FIG. 3. As can be seen, the relationship between $\ln(T_1)$ and $\ln(T_2)$ is a linear function, and the parametric slope (PS) is determined as the value of tangent of the angle between the line 41 and the abscissa axis. It can be appreciated that for determination of the PS, for example, a known linear regression algorithm can be used. For the example shown in FIG. 4, PS=0.9.

According to the invention, for determination of a desired blood characteristic certain reference data sensitive to patient individuality should be provided. The reference data should be indicative of the desired blood characteristic as a function of the parameter derived from scattering spectral features of the medium. Such reference data can, for example, be a calibration curve defining a dependence of the PS on the desired blood characteristic. The calibration curve can be created by plotting a dependence of the PS versus the desired blood characteristic that can be obtained for the particular individual or various patients by any other known method, independent of the current measurements. It should be appreciated that for different blood characteristics the independent methods may also be different. For example, a calibration curve to be used for determining the oxygen saturation for a specific patient may, in general, be constructed by applying measurements to various patients, and/or by applying the two kinds of measurements for a single patient in a breath hold experiment using a multiple-occlusion mode.

Figure 5:
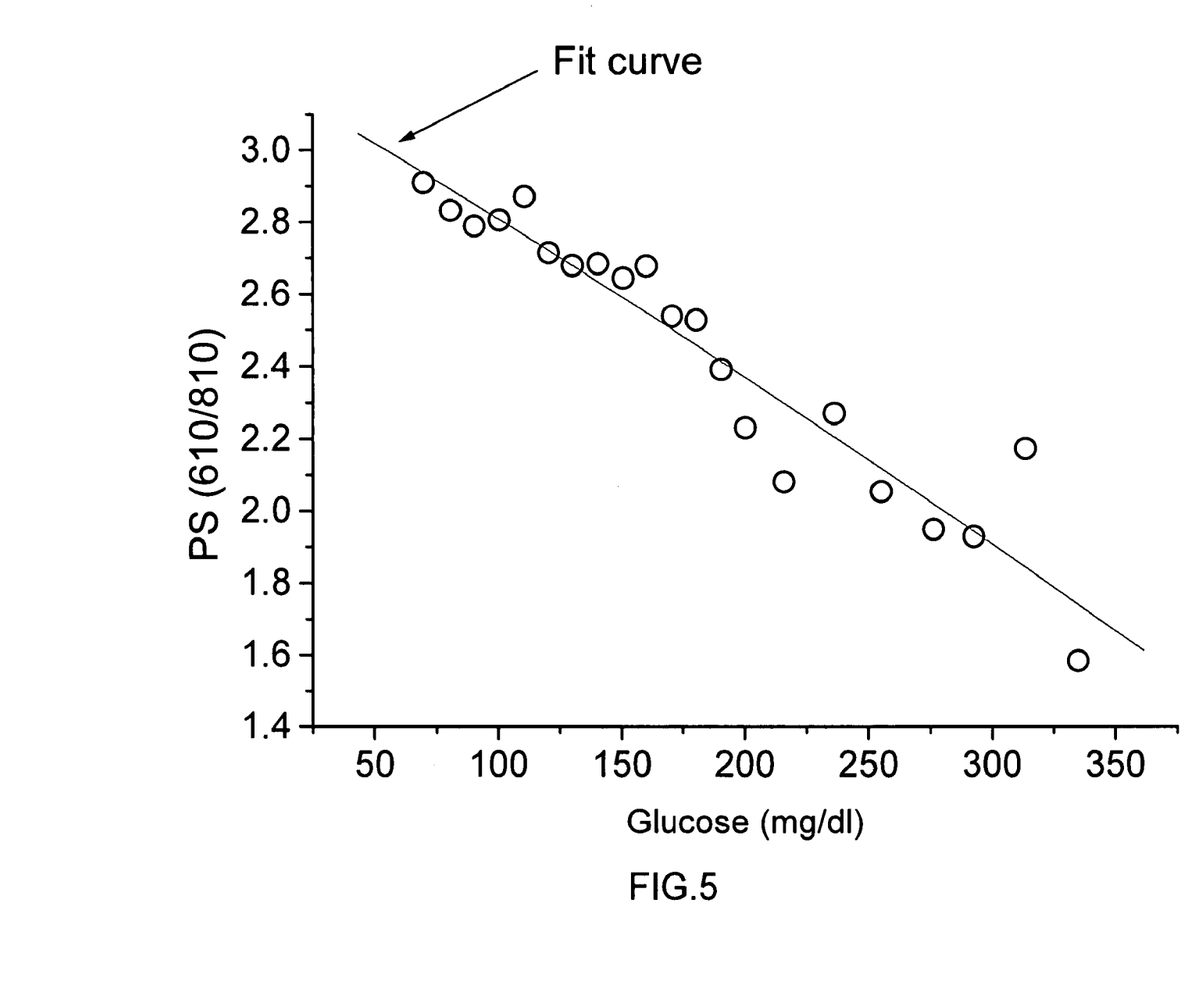
FIG. 5 illustrates an example of a calibration curve for a certain patient.

FIG. 5 illustrates an example of the calibration curve for a certain patient. This calibration curve represents a dependence of the PS calculated for the patient from the measurements of light transmission signals of the measured medium at the wavelengths $\lambda_1$=610 nm and $\lambda_2$=810 nm versus glucose concentration. This calibration curve can be used for determining a resulting value of the glucose concentration when a value of the PS is obtained by using the described above method.

It should be appreciated that the corresponding calibration curve can be obtained also for other blood characteristics. Examples of the blood characteristics include, but are not limited to concentration of a substance in patient's blood (e.g., glucose, hemoglobin), oxygen saturation, Erythrocyte Sedimentation Rate (ESR) and Erythrocyte Aggregation Rate (EAR).

Figure 6:
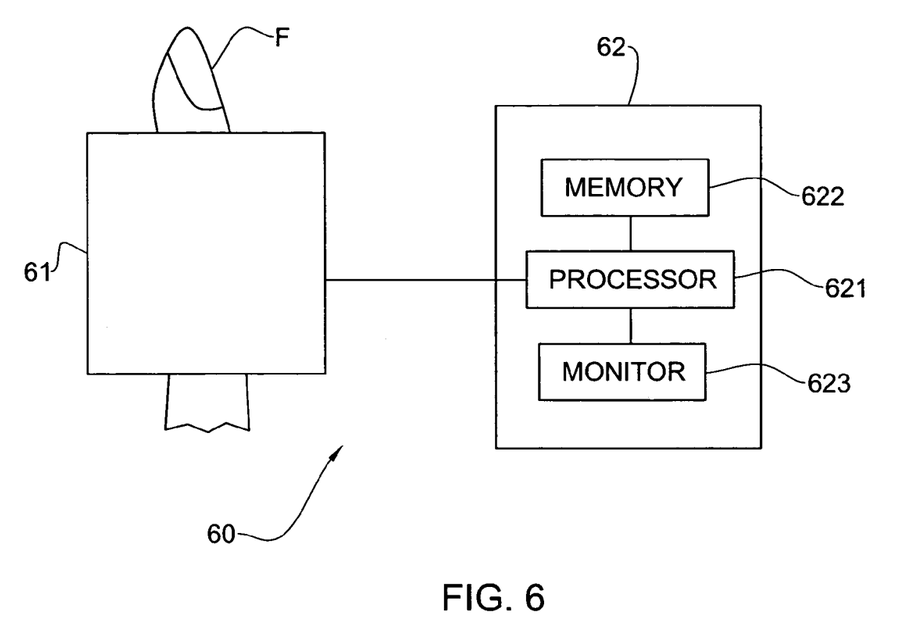
FIG. 6 illustrates a schematic block diagram of a measuring system for carrying out the method of the present invention, according to one embodiment of the invention.

Referring to FIG. 6, a schematic block diagram of a measuring system 60 applied to a patient's finger F for carrying out the method of the present invention is illustrated. It should be noted that the blocks in FIG. 6 are intended as functional entities only, such that the functional relationships between the entities are shown, rather than any physical connections and/or physical relationships. Although the application of the measuring system to the patient's finger F will be illustrated below, it should be understood that other parts of the patient's body, e.g., a toe, a wrist, an elbow and/or a knee, can also be used, mutatis mutandis, as a medium for the light transmission measurements. The system 60 comprises such main constructional parts as an optical probe 61 and a control unit 62. The optical probe 61 includes illumination and light collection/detection assemblies and a pressurizing assembly, as will be described more specifically further below with reference to FIGS. 7 and 8. The control unit 62 is connectable to the illumination assembly for operating light sources drivers, to the output of the light collection/detection assembly (via a suitable electronic block, typically including an analog to digital converter) to be responsive to measured data, and to the pressurizing assembly for controllably applying the corresponding pressure. The control unit 62 is a computer system having such utilities as a processor 621 (data acquisition and processing utility), a memory 622 for storing inter alia reference data (RD), and a monitor 623 for presenting the measurement results. The processor is preprogrammed by a suitable software model capable of analyzing the received output of the detection assembly (measured data) and determining one or more desired characteristics of the patient's blood, as have been described above.

Figure 7:
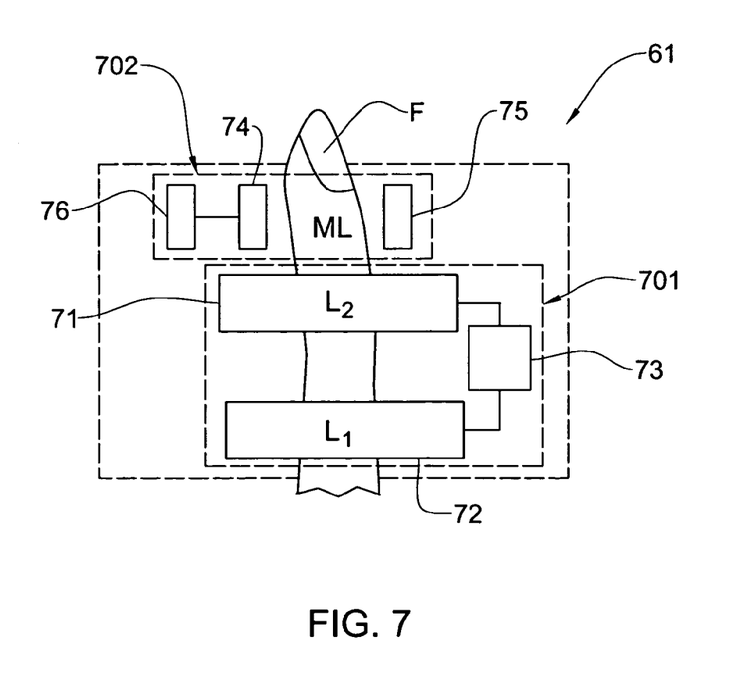
FIG. 7 illustrates a schematic block diagram of the probe schematically shown in FIG. 6, according to one embodiment of the invention.

FIG. 7 exemplifies one possible implementation of the probe 61. The probe 61 includes a pressurizing assembly 701 and a measuring unit 702. The pressurizing assembly 701 includes a primary pressurizing arrangement (occlusion cuff) 72 operable for applying the primary over-systolic pressure to the patient's finger F at a location $L_1$, a secondary pressurizing arrangement (occlusion cuff) 71 operable for applying the secondary pressure to the patient's finger at a location $L_2$ in the vicinity of a measurement location (where optical measurements are applied), and a pressure driver 73 actuated by the control unit (62 in FIG. 6) for operating the squeezing of the cuffs 71 and 72. The primary occlusion cuff 72 and the secondary occlusion cuff 71 may be of any known suitable type. It should be noted that the primary occlusion cuff 72 may, for example, be accommodated on the patient's wrist or palm, while the secondary occlusion cuff 71 and the measuring unit 702 may be located on the patient's finger. According to this embodiment, the measurement location ML and consequently the location $L_2$ of the secondary pressure, is selected downstream of the main occlusion location (location $L_1$) with respect to the normal blood flow direction.

The measuring unit 702 comprises an illumination assembly 74 and a light collection/detection assembly 75 for detecting a light response of a measurement location ML. The position of the illumination and detection assemblies 74 and 75 can be exchanged, or they can be located on the same side of the finger for reflection-mode measurements. The illumination assembly 74 is designed for generating light of different wavelengths (at least two different wavelengths). For example, the illumination assembly may include a plurality of light sources (e.g., LEDs), which are not specifically shown, associated with a suitable drive mechanism 76 operated by the control unit (62 in FIG. 6). Alternatively, a single broad band illuminator can be used. The light collection/detection assembly 75 includes one or more frequency selective detectors. Examples of collection/detection assembly 75 include, but are not limited to, spectrophotometers and/or photodiodes typically equipped with frequency selective filters and amplifying means, which are not specifically shown. It should be noted that the measurement location ML may, for example, be accommodated so as to coincide with the location of applying the secondary pressure or slightly differ from it, depending on the kind of measured medium and/or design of the measurement probe.

The optical measurements are carried out to detect the light response of the medium (light transmitted through the medium or the light reflected therefrom, as the case may be), and to generate data representative thereof (constituting measured data). In the present example of FIG. 7, the light transmitted through the medium is detected.

Figure 8:
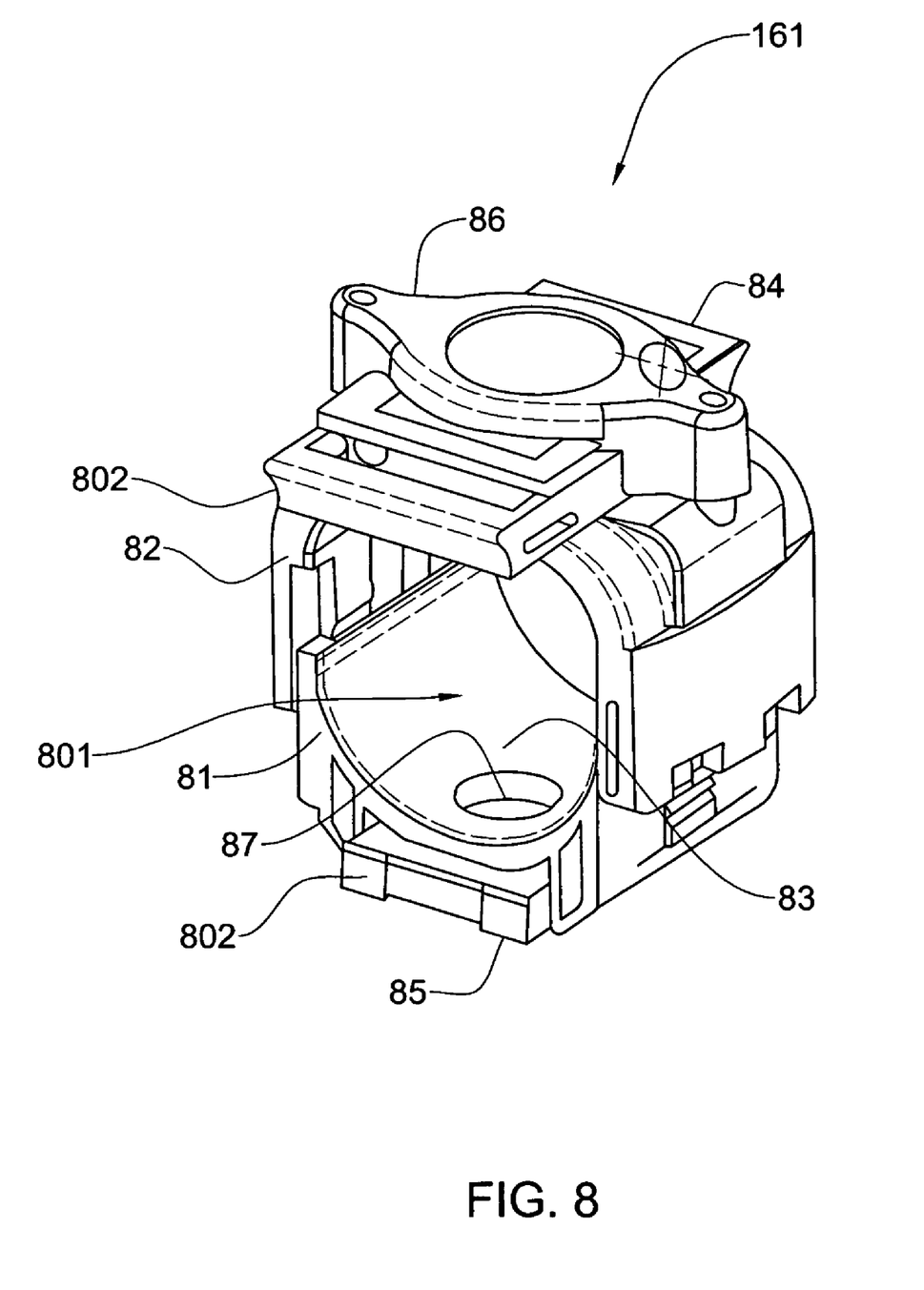
FIG. 8 illustrate a perspective view of the probe schematically shown in FIG. 6, according to another embodiment of the invention.

FIG. 8 illustrates the implementation of a probe, denoted 161, according to another embodiment of the invention, wherein the locations $L_1$, $L_2$ and measurement location ML substantially coincide. According to this embodiment, the probe 161 has two portions 81 and 82 each of a substantially U-shaped cross-section arranged with respect to each other for enclosing and holding therebetween a portion of the patient's finger (not shown in FIG. 8). The U-shape parts 81 and 82 are made of a rigid or semi-rigid material, such as metal or plastic. In the cross-section, the U-shape parts 81 and 82 can, for example, be of semi-circle or semi-oval forms. The parts 81 and 82 can partially overlap over a predetermined distance. The probe 161 comprises a pressurizing assembly 801 that includes an air cushion 83 associated with a drive mechanism (not shown) and operable to apply pressure to the finger portion enclosed between the parts 81 and 82. By moving the upper and lower parts 81 and 82 of the probe towards each other, a position of a finger therebetween is fixed. Then, a locking device 86 further fixes the parts 81 and 82 to thereby apply a certain preliminary pressure to start the measurement procedure. The locking device may be implemented by any suitable known means (e.g., including a teeth arrangement and a spring assembly) and is aimed at preventing the opening of the ring-like probe. Then, a cushion 83, which in the present example is associated with the lower semi-ring 81, is operated to press the finger to the upper semi-ring 82 to thereby apply an over-systolic pressure (e.g., 220-250 mm Hg) to thereby create a blood flow cessation in the finger and enable measurements. Then, a higher secondary pressure is supplied through the cushion 83. Thus, according to this embodiment of the invention, the primary over-systolic pressure as well as the secondary pressure is applied to the same location on the finger via the same pressurizing assembly (cushion 83). Therefore, the location of the main occlusion providing the over-systolic pressure coincides with the location at which the artificial blood kinetics is altered.

The probe 161 further comprises a measuring unit 802 configured for illuminating a measurement location on the portion of the finger with incident light beams, detecting light responses of the medium (at different wavelengths of incident light), and generating measured data indicative of time evolutions of the light responses of the blood. As described above, incident light beams being of at least two different wavelengths in a range where the scattering properties of blood are sensitive to the light radiation. The measuring unit 802 includes an illumination assembly 84 mounted on a holding frame 84 and a light collection/detection assembly 85. Similar to the previously described example, the illumination assembly 84 can include a plurality of light sources (e.g., LEDs) associated with a suitable drive mechanism (not shown) operated by the control unit (62 in FIG. 6), or a single broad band illuminator. The light sources radiate the measurement location of the finger through an aperture (not seen in FIG. 8) arranged in the part 82 to provide unobstructed optical transmission to the surface of the finger.

The light collection/detection assembly 85 includes a detector, which is not specifically shown, that can receive the light radiation transmitted through the finger via an aperture 87. In the example of FIG. 8, the measuring unit 802 operates in the transmission mode. Thus, the light collection/detection assembly 85 is mounted opposite to the illumination assembly 84. Although in the examples of FIGS. 7 and 8 the transmission mode of measurements is illustrated, it should be understood that the reflection mode of measurements can be used as well, for the purpose of which the light collection/detection assembly would be accommodated adjacent to the illuminator. Still alternatively, the detector unit may include an array of light detectors (generally, at least two such detectors) arranged in a spaced-apart relationship along the circumference of the finger.

It should be noted that the pneumatic mechanism of a pressurizing assembly may be replaced by any other suitable means. For example, a pressurizing assembly can include a squeezing cuff associated with a pressure drive (e.g., a wind-up spring) operable to move either one of the U-shape parts 81 and 82 towards one another, and thereby apply continuously variable pressure to the finger portion enclosed between the parts 81 and 82. The pressure applied to the finger should be sufficient to cause total cessation of the blood flow in the finger. Preferably, the curvature of the inner walls of the parts 81 and 82 is correlated to the average curvature of the finger such that to provide a uniform pressure on the finger along its circumference.

Those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Also, it is to be understood that the phraseology and terminology employed herein are for the purpose of description and should not be regarded as limiting.

In the method claims that follow, alphabetic characters numerals used to designate claim steps are provided for convenience only and do not imply any particular order of performing the steps.

Finally, it should be noted that the word "comprising" as used throughout the appended claims is to be interpreted to mean "including but not limited to".

It is important, therefore, that the scope of the invention is not construed as being limited by the illustrative embodiments set forth herein. Other variations are possible within the scope of the present invention as defined in the appended claims and their equivalents.

What is claimed is:

1. A system for use in non-invasive optical measurements in a human body, the system comprising:
    a probe configured as a ring-like device for removable mounting onto a patient's finger so as to enclose and hold a portion of a patient's blood perfused flesh medium between two semi-ring portions, said probe carrying a pressurizing assembly and carrying an optical measuring unit, the measuring unit being configured and operable for performing optical measurement and comprising an illumination assembly for illuminating a measurement location on the finger with incident light beams of at least two different wavelengths and a detection assembly configured and operable for detecting at least two light responses of the medium for said at least two different wavelengths, and generating at least two measured data portions indicative of said light responses; and
    a control unit configured for operating the pressurizing assembly to apply over-systolic pressure to said measurement location and maintain the application of over-systolic pressure during a certain time period, and for operating the measuring unit to perform said optical measurement during said certain time period, said control unit being preprogrammed for receiving and analyzing said at least two measured data portions, determining time evolutions of the light responses, determining a relation between said time evolutions indicative of at least one parameter of the patient's fleshy medium, and displaying said at least one parameter.

2. The probe of claim 1, wherein the pressurizing assembly is carried on an inner surface of the ring-like probe and the optical measuring unit is carried on an outer surface of said ring-like probe such that light propagating in between the optical measuring unit and the finger pass through apertures made in the ring-like probe.

3. The probe according to claim 2, wherein the pressurizing assembly comprises an air cushion assembly connected to a drive operable by the control unit to apply said over-systolic pressure to the portion of the finger covered by said air cushion.

4. The probe according to claim 3, wherein said air cushion assembly is configured and operable for applying a primary over-systolic pressure to the finger.

5. The probe according to claim 4, wherein said air cushion assembly is configured and operable for applying a secondary pressure variable up to over-systolic pressure values.

6. The probe according to claim 2, wherein the aperture associated with the light detection unit is located with respect to the aperture associated with the illumination unit so as to detect light reflected from the finger.

7. The probe according to claim 6, wherein an additional aperture associated with the light detection unit is located opposite the aperture associated with the illumination unit so as to detect light transmitted through the finger.

8. The probe according to claim 2, wherein the aperture associated with the light detection unit is located with respect to the aperture associated with the illumination unit so as to detect light transmitted through the finger.

* * * * *